United States Patent [19]

Shell

[11] Patent Number: 5,007,790

[45] Date of Patent: Apr. 16, 1991

[54] SUSTAINED-RELEASE ORAL DRUG DOSAGE FORM

[75] Inventor: John W. Shell, Hillsborough, Calif.

[73] Assignee: DepoMed Systems, Inc., Hillsborough, Calif.

[21] Appl. No.: 336,440

[22] Filed: Apr. 11, 1989

[51] Int. Cl.$^5$ .............................. A61K 9/48
[52] U.S. Cl. ................... 424/451; 424/456; 424/458; 424/464; 424/497; 424/78
[58] Field of Search ............... 424/451, 456, 458, 497, 424/78

[56] References Cited

U.S. PATENT DOCUMENTS

| | | |
|---|---|---|
| 3,435,110 | 3/1969 | Nichols . |
| 3,888,975 | 6/1975 | Ramwell . |
| 3,901,232 | 8/1975 | Michaels et al. . |
| 4,001,388 | 1/1977 | Shell . |
| 4,055,178 | 10/1977 | Harrigan . |
| 4,180,646 | 12/1979 | Choi et al. . |
| 4,207,890 | 6/1980 | Mamajek et al. . |
| 4,452,862 | 6/1984 | Markert et al. ............... 424/497 |
| 4,501,264 | 2/1985 | Rockey . |
| 4,649,043 | 3/1987 | Urquhart . |
| 4,711,783 | 12/1987 | Huc et al. . |
| 4,758,436 | 7/1988 | Caldwell et al. . |
| 4,767,627 | 8/1988 | Caldwell et al. . |
| 4,780,320 | 10/1988 | Baker . |

FOREIGN PATENT DOCUMENTS 2328580 1/1974 Fed. Rep. of Germany .

OTHER PUBLICATIONS

Mojaverian et al., (1987), Clin. Pharmacol. Ther., pp. 11–17.
Choulis et al., (1976), Pharmazie 31: 466–470.
El-Samaligy et al., (1983), J. Pharm. Pharmacol 35: 537–539.
Gilbert et al., (1987), PAP Am. Chem. Soc. 194(0), abstract no. 51.

Primary Examiner—Merrell C. Cashion, Jr.
Assistant Examiner—Leon R. Horne
Attorney, Agent, or Firm—Irell & Manella

[57] ABSTRACT

Sustained-release oral drug-dosage forms that release drug in solution at a rate controlled by the solubility of the drug are described. The dosage form comprises a tablet or capsule which comprises a plurality of particles of a dispersion of a limited solubility drug in a hydrophilic, water-swellable, crosslinked polymer that maintains its physical integrity over the dosing lifetime but thereafter rapidly dissolves. Once ingested, the particles swell to promote gastric retention and permit the gastric fluid to penetrate the particles, dissolve drug and leach it from the particles, assuring that drug reaches the stomach in the solution state which is less injurious to the stomach than solid-state drug.

9 Claims, No Drawings

SUSTAINED-RELEASE ORAL DRUG DOSAGE FORM

TECHNICAL FIELD

This invention is in the general field of pharmacology and relates specifically to an oral sustained-release drug dosage form that is retained well in the stomach and releases drug as a solution into the stomach.

BACKGROUND ART

There is an enormous amount of literature relating to oral dosage forms, including literature relating to the use of swellable polymers therein and the relationship between dosage form size and gastric retention. It is believed, however, that the field has failed to provide an oral dosage form that enables controlled release, prolonged gastric retention, and assurance that the drug is presented to the gastric mucosa as a solution rather than as the more irritating solid state. A description of representative art involving oral dosage forms using swellable polymers follows.

U.S. Pat. No. 3,435,110 describes pharmaceutical tablets composed of a mixture of uncrosslinked or crosslinked collagen fibrils and drug. In the uncrosslinked version, upon ingestion the collagen fibrils swell, rupture the tablet, and form a gel-like diffusion matrix from which drug is released slowly. In the crosslinked version, the fibrils do not swell upon ingestion but instead are enzymatically digested and apparently release drug by an erosion rather than diffusion mechanism.

Choulis, N. H., et al., Pharmazie (1976) 31:466-470, describe the formulation of tablets containing hydrophilic gums such as carbomer. Upon ingestion, the surface of the gum swells to form a zone that acts as a barrier to penetration of gastric fluid into the tablet interior. Release of drug from the tablet is said to be by erosion of the gum rather than by diffusion or some other mechanism.

DISCLOSURE OF THE INVENTION

The invention provides an oral drug dosage form that (1) provides sustained and controlled release of drug, (2) is retained well in the stomach, and (3) releases drug into the stomach in solution phase rather than the sometimes more irritating solid phase. These features make the invention dosage forms particularly useful for delivering drugs, such as antacids, that act locally within the stomach and are most effective when presented over a prolonged time period, and drugs, such as certain analgesics, that irritate the gastrointestinal mucosa when delivered in solid phase.

More particularly, the invention is an oral drug dosage form for releasing a solution of drug into the stomach over a sustained time period comprising: a plurality of solid particles composed of a solid-state drug dispersed within a hydrophilic, water-swellable polymer that (i) swells in gastric fluid to increase the particle size to a level that promotes retention in the stomach over the time period, (ii) permits slow dissolution of the dispersed drug by gastric fluid and release of the resulting solution from the particles thus assuring that only drug in solution reaches contact with the gastric mucosa, and (iii) maintains its physical integrity over at least a substantial portion of the time period and thereafter rapidly dissolves; and means for maintaining the particles prior to their ingestion in the form of a packed mass which rapidly dissolves in gastric fluid after ingestion to permit the particles to disperse within the stomach.

MODES FOR CARRYING OUT THE INVENTION

The dosage forms of the present invention may be used to administer drugs of limited solubility in gastric fluid that are capable of acting locally within the gastrointestinal tract or systemically by absorption into circulation via the gastrointestinal mucosa. The drug should be solid and not so water soluble that it is rapidly leached from the particles over a very short time, i.e., less than about four hours, nor so insoluble that too little is leached from the particles to achieve the desired therapy. Thus, drugs having a solubility that permits them to dissolve and leach from the particles at a rate that provides the pharmacokinetics needed for improved therapy and the desired duration of treatment are selected. Normally, the solubility of the drug (measured in water at 37° C.) will be in the range of about 0.001% to about 35% by weight, preferably 0.001% to 5% by weight.

The invention is particularly useful for delivering antacid agents locally to the stomach so that their neutralizing activity is extended or drugs that are irritating to the gastrointestinal tract when introduced to the mucosa as a solid. Specific examples of drugs that may be administered via the invention dosage form are antacids/anti-ulcer agents such as calcium carbonate; $H_2$-antagonists such as cimetidine and ranitidine; anti-arthritic (anti-inflammatory) agents such as indomethacin, ibuprofen, naproxen, prednisone, prednisolone, dexamethasone, and piroxicam; analgesics such as aspirin; calcium channel blockers such as nifedipine; and potassium supplements such as potassium chloride. The invention is especially advantageous with the mentioned anti-arthritic and analgesic agents since these agents may be highly injurious to the gastrointestinal tract, to the extent that they sometimes cause bleeding when they are administered in conventional dosage forms in which the drug in its solid state contacts the mucosal tissue.

The drug is dispersed in a hydrophilic, water-swellable polymer that dissolves in gastric fluid in a predictably delayed manner. This combination of properties—water swellability and a "programmed eventual dissolution"—permit the dosage form to perform in accordance with the invention. The hydrophilicity and water swellability cause the drug-polymer particles to swell in size and permit the ingress of gastric fluid into the particle. The relationship between the solubility of the drug in gastric fluid and the diffusivity of the drug through the swollen polymer is such that the release rate of drug from the particle is primarily controlled by the dissolution rate of the drug in gastric fluid, which in turn is a function of its equilibrium solubility in the fluid. The release rate is thus primarily dependent upon the rate at which the poorly soluble drug is leached, via slow dissolution rate, from the particle. Correlatively, because the polymer maintains its integrity (i.e., it does not significantly or appreciably dissolve, erode or otherwise decompose or degrade) over at least a substantial portion (i.e., at least about 90% and preferably over 100%) of the intended dosing period and only thereafter dissolves, drug is not released into the stomach in solid form nor is there any significant drug release via erosion. The polymer should normally undergo extensive physical dissolution within 4 to 8 hours after the end of the dosage period due to cleavage of crosslinks—a delayed reaction that occurs rapidly once initiated.

The programmed eventual dissolution of the polymer depends upon the nature of the polymer and the degree of crosslinking. The polymer is nonfibrillar and substantially water soluble in its uncrosslinked state, and the degree of crosslinking is sufficient to enable the polymer to remain insoluble for the desired time period, normally at least from about 4 hours to 8 hours up to 12 hours, with the choice depending upon the drug incorporated and the medical treatment involved. Examples of suitable crosslinked polymers that may be used in the invention are gelatin, albumin, sodium alginate, carboxymethyl cellulose, polyvinyl alcohol, and chitin. Depending upon the polymer, crosslinking may be achieved by thermal or radiation treatment or through the use of crosslinking agents such as aldehydes, polyamino acids, metal ions and the like.

The drug/polymer mixture is in the form of a plurality of particles. The drug is preferably dispersed homogeneously in the polymer, although it need not be. The weight ratio of drug to polymer in the mixture or dispersion will normally be 1:4 to 2:1, preferably 1:2 to 1:1, and most preferably 2:3 to 1:1. The particles are preferably spherical in shape, but may be in the shape of less regular, but equant, granules. The swollen particles will be of a size that promotes their retention in the stomach. This will normally be in the range of about 1 to about 3 mm (measured as the diameter for spherical particles or largest dimension for irregularly shaped particles), but may be larger. Since the particles will typically swell at least 50% of their original volume, the initial particle size is usually in the range of about 50 microns to 2 mm, preferably 0.5 to 1.5 mm. Because the particles retain their physical integrity during the dosing period, their swollen volume will remain substantially constant (i.e., typically less than a 25% decrease) over the dosing period.

The drug/polymer mixture may be made by conventional techniques used to make microspheres (e.g., forming a drug-monomer/prepolymer emulsion followed by crosslinking) or by conventional mixing, forming, and comminution techniques. Each unit dosage form of the invention contains a plurality of particles, normally between about $3 \times 10^2$ and $4 \times 10^5$, and preferably between $4 \times 10^2$ to $2 \times 10^3$.

The particles may be formed into a packed mass for ingestion by conventional techniques. For instance, the particles may be encapsulated as a "hard-filled capsule" or a "soft-filled capsule" using known encapsulating procedures and materials. The encapsulating material should be highly soluble so that the particles are rapidly dispersed in the stomach after the capsule is ingested. Alternatively, the particles may be formulated with a soluble binder and compressed into a tablet or pill.

Drug-release patterns may be altered by varying the encapsulating/binder material to retard dispersal of the particles or by coating the particles with drug to achieve an initial burst or bolus of drug release.

The following examples further illustrate the invention. These examples are not intended to limit the invention in any manner.

EXAMPLE 1

Thirty grams of gelatin are added to 50 cc of distilled water, and the mixture is allowed to stand at 25° C. for one hour while the gelatin hydrates and swells. To this mixture are added 20 grams of calcium carbonate, and the preparation is heated to 60° C. while it is stirred at 300 rpm for 30 minutes to effect dissolution of the gelatin and to assure even suspension of the calcium carbonate. Additional distilled water previously heated to 60° C. is then added to bring the total volume to 100° C. while the stirring is continued. This preparation is slowly poured into 400 cc of a mixture consisting of 20% by volume of corn oil in petroleum ether, which has previously been heated to 60° C., while the petroleum ether solution is stirred at 500 rpm. This preparation is then cooled to 5° C. with continued stirring, and the stirring is continued at 500 rpm for one hour after the lower temperature is reached. Two hundred cc of isopropanol are then added while stirring of the preparation at 5° C. is continued. The solid microspheres are then collected by filtration and washed three times with isopropyl alcohol. The capsules are then immersed in 50 cc of a 1% solution of glutaraldehyde in isopropyl alcohol for eight hours at 5° C., then washed again three times with isopropyl alcohol, filtered, and vacuum dried for 24 hours. The microspheres, which average between 200 and 300 microns in diameter, are filled into gelatin capsules for administration as a long-acting antacid product (1.5 grams of the microsphere mix, which contains 600 mg calcium carbonate, are filled into each size O capsule). The microcapsules, when released into the stomach following ingestion, delay the reaction of the calcium carbonate with the acid of the stomach for a useful period of time (between three and six hours), which provides for sustained antacid protection for the patient. Physical integrity of the matrix is maintained for from one to four hours after the release of its drug contents, after which the matrix dissolves through hydrolytic cleavage of its bonds and proteolytic digestion.

EXAMPLE 2

The procedure of Example 1 is followed except that the 20 grams of calcium carbonate is replaced with 30 grams of potassium chloride, and the making of the microspheres is the same as in the first example. The 1.5 grams of microspheres thus produced are filled into each size OO capsule. This final dosage form delivers a total dose of 600 mg KCl, but over a sustained time period of from one to four hours and in such a way that the potassium chloride is in the solution state, rather than the more injurious solid state, when it contacts the gastrointestinal mucosa. Total dissolution of the microspheres occurs from one to five hours after the drug content is depleted.

EXAMPLE 3

Thirty grams of gelatin are added to 50 cc of distilled water and the mixture allowed to stand at 25° C. for one hour while the gelatin hydrates and swells. This preparation is then heated to 60° C. while it is stirred at 300 rpm for 30 minutes. Forty cc of distilled water previously heated to 60° C. are then added and the solution stirred at 500 rpm for an additional five minutes. Twenty grams of finely powdered aspirin are then added to the solution while stirring is continued to give a uniform suspension. After one minute the warm suspension is poured without delay into 400 cc of a rapidly stirred (500 rpm) solution of 20% corn oil in petroleum ether, which has been previously brought to 25° C., and the resulting emulsion is rapidly (i.e., over a period of no more than 5 minutes) cooled to 5° C. while the stirring is continued. Two hundred cc of cold (5° C.) isopropyl alcohol are then added to dehydrate the gelatin microspheres while the preparation is stirred for another ten minutes. The microspheres are then collected by filtration and washed three times with cold (5° C.) isopropyl alcohol. They are then immersed in 50 cc of a 1% solution of glutaraldehyde in cold (5° C.) isopropyl alcohol for 8 hours, then washed three times with isopropyl alcohol, collected by filtration, and vacuum dried for 24 hours. The microspheres, which average 300 to 400 microns in diameter, are filled into gelatin capsules for administration as a safer, long-acting, analgesic product (800 mg of the microsphere mix, which contains 320 mg of aspirin, is filled into each size O capsule). The capsules, when released into the stomach following ingestion, provide for sustained release of the drug for from one to four hours and also assure that the drug reaches the gastrointestinal mucosa while in the solution state, rather than the more deleterious solid state that is characteristic of conventional dosage forms of this drug. Physical integrity of the matrix is maintained for from one to four hours after release of its drug content, after which time the matrix dissolves.

EXAMPLE 4

Three grams of sodium alginate are dissolved in 100 cc distilled water at 25° C., and 2 grams of cimetidine are added to this solution with constant mixing. This preparation is added dropwise to a 2% calcium chloride solution through a small orifice that delivers droplets 1.0 mm in diameter. The spherical beads of cimetidine-containing calcium alginate thus formed are collected by filtration and washed three times with distilled water. The beads are then immersed in a 0.05% aqueous solution of poly-L-lysine (molecular weight 14,000) for four hours, then washed again three times with distilled water, collected by filtration, and dried under vacuum for 24 hours. The beads thus produced are filled into gelatin capsules (800 mg per capsule, providing a dose of 275 mg of cimetidine). This dosage form for the delivery of cimetidine over an extended time period allows for through-the-night protection of patients who suffer from excess gastric acidity without the high bedtime dose that conventional dosage forms require for this duration of protection. The high bedtime dose otherwise required for such protection is associated with untoward side effects, which are reduced through use of the dosage form described in this example.

EXAMPLE 5

A mixture consisting of 20 grams of ibuprofen previously triturated in 10 cc glycerin is added with rapid stirring to an aqueous solution consisting of 20 grams (w/v) of sodium alginate in 1 liter of distilled water. This solution is then added to 2 liters of a 2% (w/v) zinc chloride solution which has previously been adjusted to pH 3 by the addition of HCl while the rapid stirring is continued for 10 minutes. The preparation is then allowed to stand at room temperature for four hours, after which the drug-entrapped zinc alginate precipitate is collected by filtration, washed three times with distilled water, and dried under vacuum for 24 hours. After drying the residue is granulated using minimal amounts of glycerin/water and processed into 0.5 mm diameter microspheres by mechanical extrusion and spheronization. Fur this purpose, use is made of a Nica Extruder (Aeromatic Ltd., Bubendorf, Switzerland), into which the slightly flexible mass represented by the above residue is fed, and which produces therefrom a continuous flow of cylindrical extrudate 0.5 mm in diameter. This extrudate falls onto the spinning plate of a Nica Spheronizer (Aeromatic Ltd.), where it is broken into cylinders of approximately 1:1 length:diameter ratio. Interaction then between the spinning disc and the wall of the spheronizer causes the cylinders to be worked into spheres of 0.5 mm diameter. The spheres are then filled into gelatin capsules (1 gram of spheres per size O capsule, which represents a total dose of 450 mg ibuprofen). The capsules of spheres thus produced represent a sustained-release dosage form for analgesic-antipyretic activity with less propensity for gastrointestinal side effects than the conventional tablet form of ibuprofen. Upon ingestion the spheres begin to release the incorporate drug almost immediately but begin erosion in from three to five hours. Total erosion time is approximately eight hours.

EXAMPLE 6

The procedure of Example 5 is followed, except that the 20 gram amount of the drug in Example 5 is replaced with 2 grams of indomethacin; the total resulting dose in the indomethacin formulation is 45 mg.

Modification of the above-described modes of the invention that are obvious to those of skill in the field of pharmacology, drug delivery, polymer chemistry and related fields are intended to be within the scope of the following claims.

I claim:

1. A sustained-release oral drug dosage form for releasing a solution of drug into the stomach comprising:
   a plurality of solid particles of a solid-state drug dispersed within a hydrophilic, water-swellable polymer that (i) swells via imbibition of gastric fluid to increase the particle size to a level that promotes retention in the stomach over said time period, (ii) permits dissolution of the dispersed drug by imbibed gastric fluid while the drug is within the particle and release of the resulting solution via a leaching action from the particles, thus assuring that drug only in solution reaches contact with the gastric mucosa, and (iii) maintains its physical integrity for at least a substantial portion of the time period during which the drug is released into he stomach and thereafter rapidly dissolves,
   wherein said drug is selected from the group consisting of calcium carbonate, cimetidine, ranitidine, indomethacin, ibuprofen, naproxen, prednisone, prednisolone, dexamethasone, piroxicam, aspirin, nifedipine, and potassium chloride,
   and wherein said polymer is selected from the group of polymers consisting of crosslinked gelatin, crosslinked albumin, crosslinked sodium alginate, crosslinked carboxymethylcellulose, crosslinked polyvinyl alcohol, and crosslinked chitin,
   and wherein said dosage form is in the form of a tablet or capsule that maintains the particles in a packed mass prior to their ingestion and then rapidly disintegrates in gastric fluid to permit the particles to disperse in the stomach after their ingestion.

2. The dosage form of claim 1 wherein the sustained time period is 2 to 6 hours.

3. The dosage form of claim 1 wherein the substantial portion is at least 90% of the time period.

4. The dosage form of claim 3 wherein the polymer dissolves within 4 to 8 hours of the end of such substantial portion of the time period.

5. The dosage form of claim 1 wherein the swollen size of the particles is about 1 to 3 mm.

6. The dosage form of claim 5 wherein the unswollen size of the particles is about 50 microns to 2 mm.

7. The dosage form of claim 1 wherein the solubility of the drug in water at 37° C. is 0.001% to 35%.

8. The dosage form of claim 1 wherein the drug is aspirin.

9. The dosage form of claim 8 wherein the polymer is crosslinked gelatin.

* * * * *